(12) United States Patent
Oliveira Neto

(10) Patent No.: US 11,458,314 B2
(45) Date of Patent: Oct. 4, 2022

(54) METHOD FOR CONFIGURING AN ELECTROANALGESIA AND ELECTROTHERAPY APPARATUS

(71) Applicant: Jeronimo Manço De Oliveira Neto, Ribeirão Preto (BR)

(72) Inventor: Jeronimo Manço De Oliveira Neto, Ribeirão Preto (BR)

( * ) Notice: Subject to any disclaimer, the term of this patent is extended or adjusted under 35 U.S.C. 154(b) by 0 days.

(21) Appl. No.: 16/958,852

(22) PCT Filed: Mar. 28, 2018

(86) PCT No.: PCT/BR2018/050085
§ 371 (c)(1),
(2) Date: Jun. 29, 2020

(87) PCT Pub. No.: WO2019/126846
PCT Pub. Date: Jul. 4, 2019

(65) Prior Publication Data
US 2021/0069506 A1 Mar. 11, 2021

(30) Foreign Application Priority Data
Dec. 29, 2017 (BR) ............... 10 2017 028618 5

(51) Int. Cl.
*A61N 1/36* (2006.01)

(52) U.S. Cl.
CPC ....... *A61N 1/36021* (2013.01); *A61N 1/3603* (2017.08)

(58) Field of Classification Search
CPC .................. A61N 1/36021; A61N 1/3603
USPC ............................................. 607/46
See application file for complete search history.

(56) References Cited

U.S. PATENT DOCUMENTS

2006/0085049 A1* 4/2006 Cory ............... A61B 5/0536
607/48

* cited by examiner

*Primary Examiner* — Nadia A Mahmood
(74) *Attorney, Agent, or Firm* — Maier & Maier, PLLC

(57) ABSTRACT

A method for configuring an electroanalgesia and electrotherapy apparatus using wireless control, with multiple stimulators, particularly used in the segment of pain control and aid in postoperative tissue repair and reduction of measures and body weight. According to the embodiments, a user with electrodes generically distributed simultaneously in several parts of the body, where at the pain site the frequency is from 80 Hz to 300 Hz or 1000 Hz and then to a range of 15 Hz to 35 Hz or among 0.5 Hz and 10 Hz on that electrode, and at distant points, for example, in upper or lower limbs the frequency is from 0.5 Hz to 10 Hz and, so the person can be submitted to this analgesia procedure, according to the pre-determined frequencies, pulse width and pulse form already pre-defined.

5 Claims, 5 Drawing Sheets

METHOD FOR CONFIGURING AN ELECTROANALGESIA AND ELECTROTHERAPY APPARATUS

FIELD

This patent application concerns a method for configuring an electroanalgesia and electrotherapy apparatus using wireless control, with multiple stimulators, particularly used in the segment of pain control and aid in postoperative tissue repair and reduction of measures and body weight.

More particularly, the invention is intended to control pain and to promote analgesia, quick and long-lasting, in different clinical procedures. Among these, pain control during tattooing, pain resulting from playing sports (before training, Furthermore, it has application as an analgesic preparation prior to and/or during invasive procedures such as dental or surgical procedures, or similarly for aesthetic purposes (facial and lip fillings, small surgeries). Additionally, useful for sports training before, during or after game activities or any type of acute pain. Another function of the invention is to assist for pain relief in chronic pain situations, such as tension pains, low back pain, muscle pain and/or cervical, thoracic or lumbar spine, Paget's disease of bone, fibromyalgia, arthritis, arthrosis, plantar fasciitis, shin splint, neuralgia, including opioid addicted dependent patients; in patients in late stages of cancer, replacing morphine, taking the caution of pacemaker users, pregnant and people with epilepsy.

BACKGROUND

It is unknown in the world market a wireless control electro-stimulator device with internal rechargeable battery, and wireless charger that can be used connected to the surface of the electrodes, which is capable of emitting at the same time electric pulses of different frequencies—low (less than 10 Hz), medium (around 15 Hz to 35 Hz) and high (between 100 and 1000 Hz)—which are considered therapeutic since they promote cell action potential (nerve transmission), increase local blood vascularization, drain extracellular fluids into blood and lymph vessels—alternating pulses frequencies, so that the wave is compensated rectangular pulse (or with inverted exponential), non-polarized or inverted biphasic, with a pulse width from 1 ms—1 millisecond—(1000 μs) to 2 ms (2000 μs) at all frequencies and maximum wave amplitude of 100 mA. This configuration is able to quickly eliminate acute pain, even during a soft tissue surgery or to relieve cases of chronic pain, when high and low frequency are combined simultaneously in different electrodes or interspersed in the same electrode.

There are cordless devices on the market with TENS (Transcutaneous Electrical Neurostimulation) type surface electrodes, but which do not meet the requirements mentioned in the previous paragraph; as well as wired devices that do not meet the usage and operational conditions proposed in this patent application, but mainly there are no devices with multi-stimulators on the market with the possibility of using 2 or more simultaneous frequencies (wireless control and increment gradation as to be applied by this patent application—paragraph 0010).

At world market, none of the existing TENS-type cordless devices is able to completely eliminate pain, once they do not have: pulse width equal to or greater than 1 ms (1000 μs), nor the possibility of using the combination of two frequencies or more at the same time, in different outputs, as a pre-programmed (memory) setting or by programed protocols through software.

At Brazilian market, there are some electrotherapy or electroacupuncture devices that have fully adjustable parameter configurations, able to adjust a maximum of two frequencies at the same time into different outputs, with a maximum pulse width of 1000 μs at the frequency equal to or less than 10 Hz, and maximum pulse width of 800 μs above 35 Hz, however, these units connect a single device (electro-stimulator) to all electrodes by cables, (without wireless command) which makes it very difficult to use in dentistry, for example, due to dentists' needs to use electrodes with different frequencies in distant points, such as the simultaneous placement of electrodes in the regions of the head, upper limbs (arms and hands) and lower limbs (legs and feet), in addition to the dentists' needs to use the instruments and equipment close to the patient's mouth. Another drawback is the need to operate the equipment during the entire treatment period by an operator (either the professional or the patient) so that this type of equipment must be close to the operator, and since each person has a different degree of tolerance of the increasing current intensity. Current equipment with a single stimulator also generates a lack of practicality/mobility in using the equipment in non-dental situations. If cables connecting a minimum of 4 electrodes (and up to 8 electrodes) to a single piece of equipment must be kept by the operator always makes both patient and professional mobility difficult. Another deficiency of some devices is the inability to switch among different frequencies during stimulation, so that each time a frequency needs to be changed, the current intensity returns to zero, and the equipment is restarted.

Some devices do not set up waves with different frequencies on different electrodes (example: a pair of electrodes at 150 Hz and another pair of electrodes at 8 Hz). In addition, most of these devices are not indicated for use on the head, and still have a pulse width that does not reach 600 μs.

SUMMARY

The objective of the invention is to develop equipment with a set of independent electro-stimulators, using wireless control, capable of making effective and long-lasting reduction of pain by combining the electrical signals configurations previously described, in an effective, simple and practical way, non-invasive, without the use of anesthetic drugs, since these several units of electro-stimulators are connected to the electrodes (one electro-stimulator for each pair of electrodes). In addition, the high frequency (from 80 Hz to 300 Hz) is able to eliminate pain quickly, not leaving the tissue treated with the sensation of numbness or tingling after stimulus cession.

However, low frequencies below 10 Hz are able to produce long-lasting analgesia by releasing endogenous opioids (endorphins, enkephalins) that are 700 (seven hundred) times more potent than morphine and are metabolized very slowly by the body, which allows its duration for periods greater than 12 (twelve) hours, reaching pain relief of up to 72 hours after a single session. The combination of high and low frequency, simultaneously in different parts of the body, allows an effective and long-long-term effect. Clinically, this has been shown as patients without postoperative pain, edema and/or without bleeding after surgeries. Moreover, this combination may allow the patient return to consultations with a shorter time repair. Traditional healing equivalent to 7 (seven) days after surgery can be usually seen equal to 4 (four) days after a single session of electrostimulation, even in compensated and slightly decompensated diabetic patients.

The equipment has electrostimulation increments that vary in 0.1 mA graduations (between 0 mA to the 10 mA peak) and then 0.5 mA graduations/variations (between 10 mA to the 20 mA peak) and then 1 mA increases (from 20 mA to the peak of 100 mA), thus making the electrical signal more comfortable and easier to adapt on the skin, including young children or elderly people, who are more sensitive.

An advantage of the invention is the creation of a safe, fast, long-lasting, completely non-invasive, comfortable analgesic/anesthetic method, free of anesthetic drugs, through neuronal modulation of the patient, which can be used in patients with fear of injection, needles or allergic to painkillers and/or anesthetics.

Another advantage is that a non-polarized wave prevents the electrolysis of tissues (such as burns) and, therefore, its use can be used for a period of more than 1 (one) hour without any type of tissue damage, in fact with the benefit of reducing edema near the applied areas and even decreasing body weight, when applied to areas of the trunk close to the abdomen.

It is also an advantage of the invention the result obtained by the applicant from the report of all the patients as a technique that produces relaxation, since the frequency close to 100 Hz at a pulse width between 1 ms and 2 ms is capable to produce the release of serotonin, related to the pleasure sensation and well-being hormone, in addition to dopamine regulation leading to patient comfort and reduction of anxiety after treatment.

The great advantage of using pulse width between 1 ms and 2 ms is the fact that it is long enough to produce a potential action (current flow) in excitable cells such as nerve cells, which is a transient reversal of the membrane potential, in other words, a depolarization of the membrane and conduction of the nervous stimulus. Meanwhile, muscle fibers need up to 2 ms to be activated. Thus, a pulse width between 1 ms and 1.5 ms is safe to activate nerve endings without muscle contractions with lower stimulus intensity, which can be better seen in FIG. 5 which demonstrates the action potential as a function of intensity versus pulse duration. In other words, analgesia is achieved with lower intensity (compared to shorter pulse width signs) and without significant muscle contractions in the patient. This is important, for example, when the dentist needs to keep the patient with an open mouth during electroanalgesia, with the electrodes adhered to the surface of the jaw, to perform an intra-oral procedure, for example.

Another important factor lies in the patients' report of sleeping well on the days of applying this technique and waking up with the sensation of restful sleep. This feedback has been shown to be relevant, as such reported well-being has greatly influenced the reduction of patients' anxiety and fear when they return to the next consultations. In dentistry, specifically, patients have reported that the technique developed by the applicant is of first choice as prior analgesia for dental procedures of dental restoration, tooth whitening without sensitivity (during and after the procedure), soft tissue surgery, lip and facial filling, immediate relief of dental pain (canal pain—endodontics), as an adjunct in endodontic treatment, pain in inflamed tissues.

Another advantage of the equipment use is for chronic pain cases such as fibromyalgia, trigeminal neuralgia, Paget's disease of bone, and severe pain causes where it has been noted relief and improvement of sleep quality for these patients, for periods ranging from 2 days to a week, after a single session.

It is also considered an advantage for the invention the reduction of pain from muscles, tendinopathies, and muscle fascia in sportspeople, due to intense training and it has shown positive results in accelerating their recovery.

Therefore, the great advantage of the invention consists of rapid suppression of pain, achieved by combination of electrical stimulation in a safe, effective, comfortable and practical mode, with configuration of different waves simultaneously stimulating different parts of the body and wirelessly connecting the electro-stimulator to the controller.

Since the advantages of the non-invasive and comfortable method allow the patient not to feel pain and promote relaxation immediately during and after the sessions, patients have reported less fear of the dentist, and the possibility to return to the consultation in a shorter time without afflictions. Herewith, it is a great advantage of the method to control or reduce the three worst situations commonly seen at the dentist, which are PAIN, FEAR and ANXIETY.

Evidently, the invention will also include an apparatus, however, in this request, the objective is the configuration of parameters attributed in terms of associated frequencies (between 0.5 Hz to 35 Hz associated with the 80 Hz to 250 Hz interval), pulse width between 1 ms and 2 ms (from 1000 µs to 2000 µs) unprecedented of those that already exist, waveform (rectangular with inverted exponential and can also be alternating biphasic)—see FIG. 2, form of stimulation (pulsed type from continuous waves and mixed type)—see FIG. 4—considering that, according to clinical trials performed, the results obtained are a direct function of these configurations. Must be highlighted the practicality of using several electro-stimulators simultaneously at different points, with alternation of frequency during the use, at the operator's choice, associated with a remote-control command by Bluetooth, which may be a mobile or tablet application.

DETAILED DESCRIPTION OF THE EMBODIMENTS

METHOD FOR CONFIGURING AN ELECTROANALGESIA AND ELECTROTHERAPY APPARATUS, object of this Patent Application, employs an apparatus (not shown) consisting of a wireless charging base (induction) for the wireless stimulator components to be attached (also can be by wire in case of urgency in charging the battery, or to facilitate the insertion of memorized protocols, when necessary), and must contain terminals for connection between the electrodes and the electro-stimulators—these consisting of electronic plates and rechargeable batteries and a retractable cable on the body of the electro-stimulator, and a button to switch on/off (3 s pressure activation) or quick touch to switch between the installed programs—and a remote control (or mobile app), by Bluetooth, to control the intensity of the pulses, switch on and switch off, set action modes and parameters and a display for programming view.

The invention simultaneously stimulates: at the pain site (2) the frequency between 80 Hz and 200 Hz or close to 1000 Hz and then reduce to a frequency range of 15 z to 35 Hz on that electrode; and in points at a distance as in members (3) the frequency is from 0.5 Hz to 10 Hz.

Figure 2:
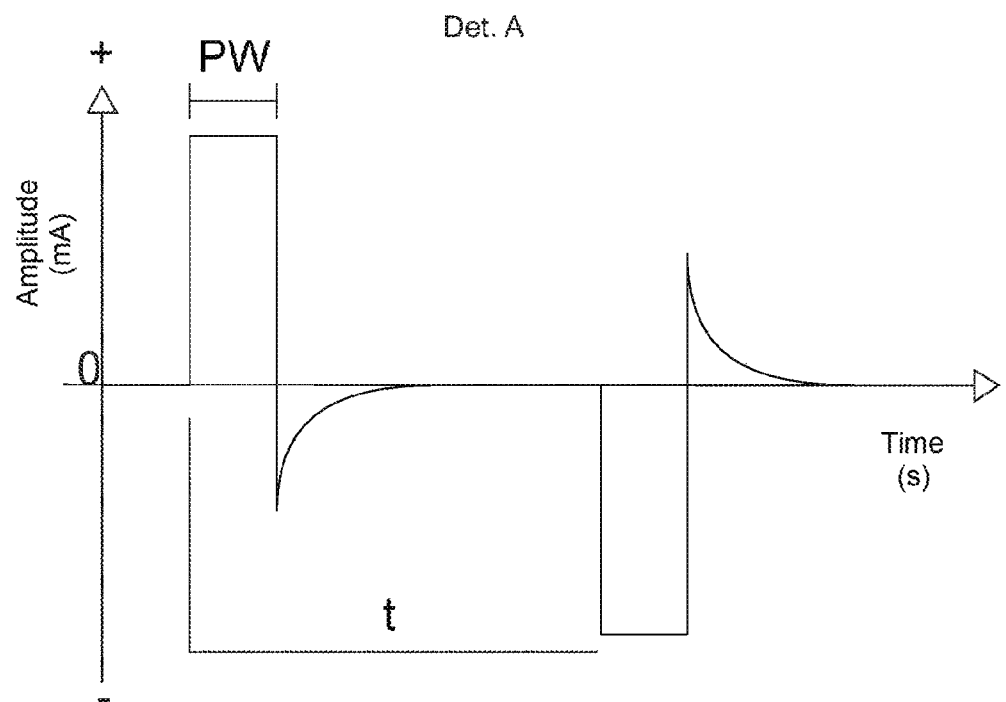
FIG. 2: A) Graph of non-polarized pulse–current (mA)× time (s) and B) Graph of inverted biphasic pulse.
Figure 2:
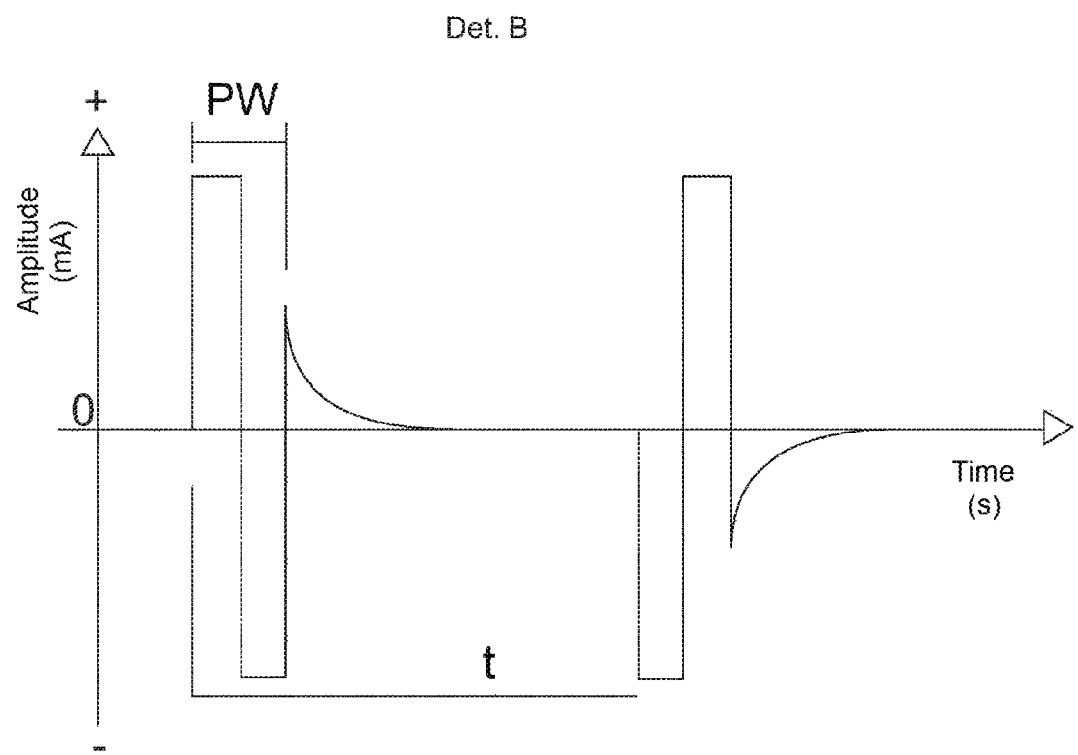
Figure 3:
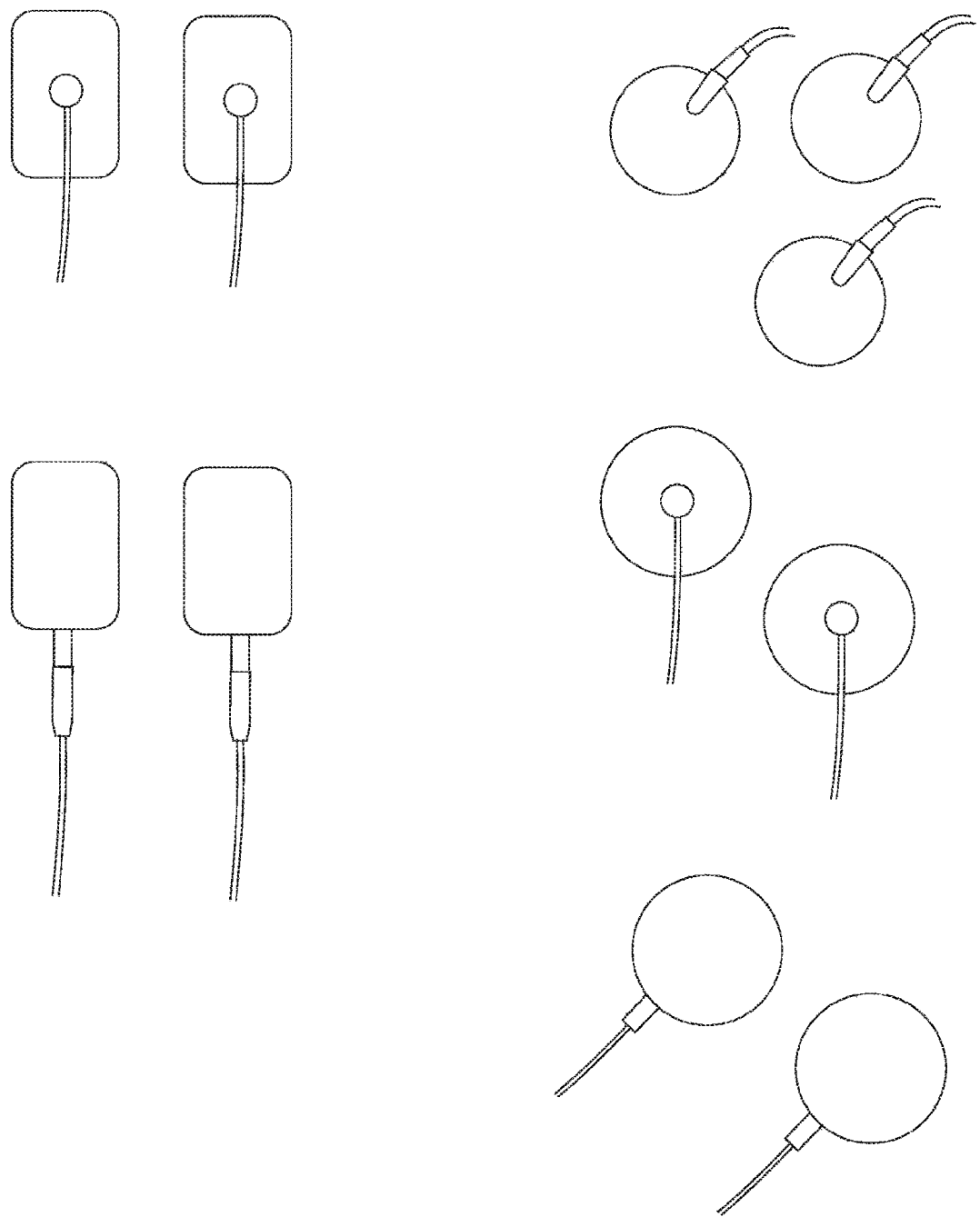
FIG. 3: Exemplification of some types of electrodes.
Figure 4:
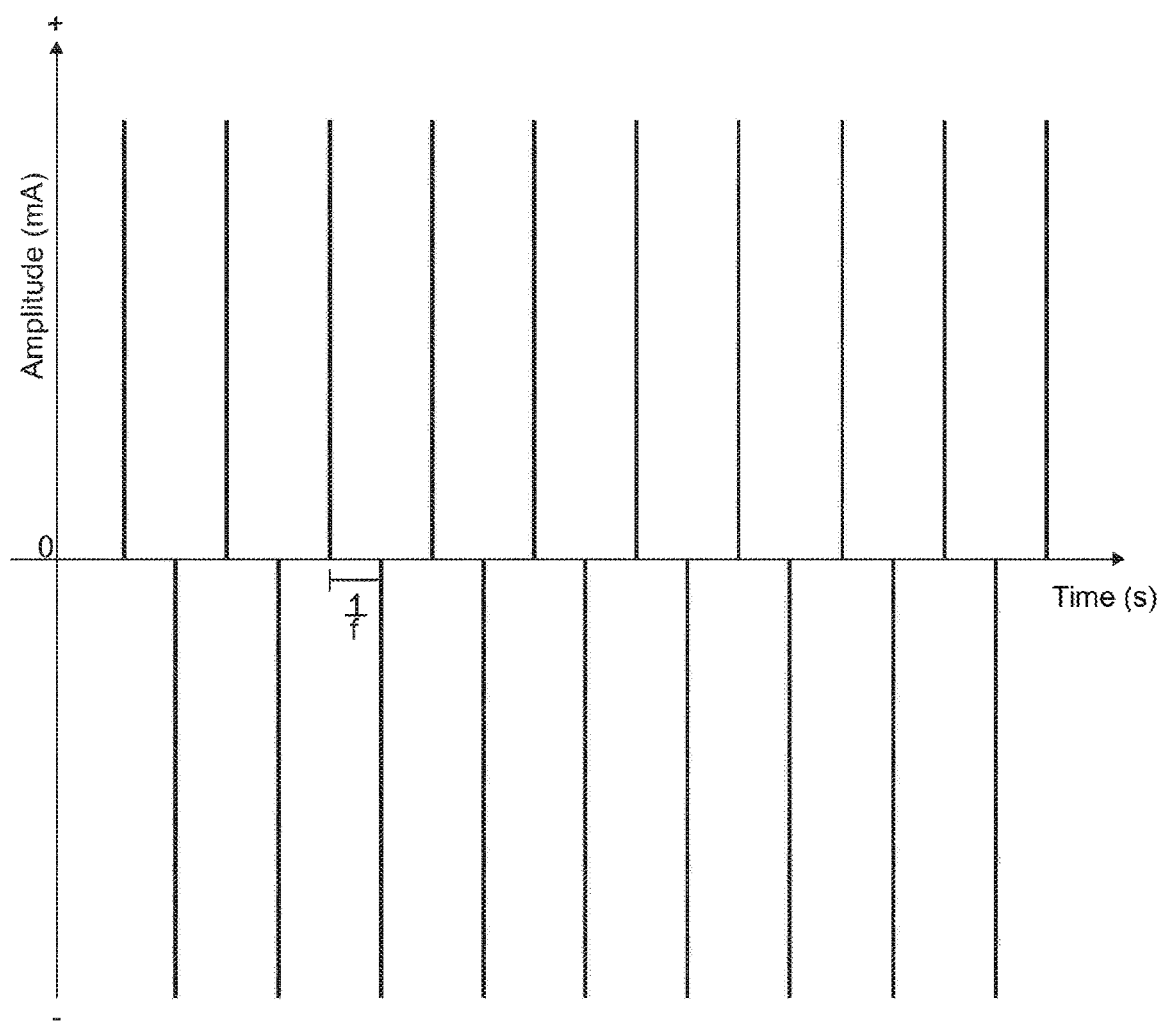
FIG. 4: Graph showing "Continuous" type stimulation.
Figure 5:
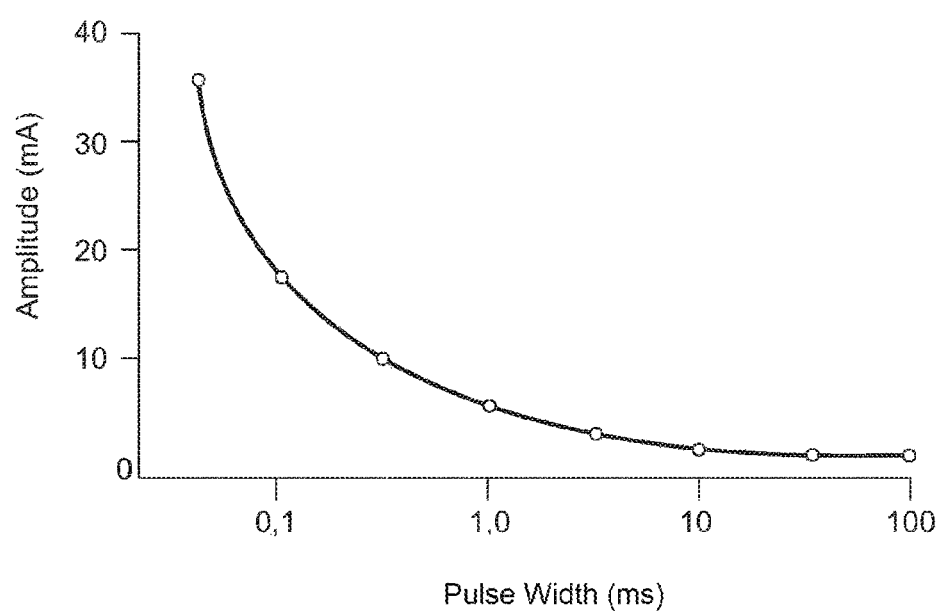
FIG. 5: Graph showing the relationship between current intensity and duration of a stimulus needed to generate an action potential in a motor nerve fiber.

FIG. 2 shows that the method of the invention performs a rectangular and non-polarized wave (4), with a pulse width of 1 ms (1000 µs) and/or greater, with a wave amplitude of up to 100 mA.

The low frequency, less than 10 Hz, with pulse width or duration close to 1 ms is capable of producing long-onset analgesia (after 20 minutes of stimulation) and long-lasting effect through the release of endogenous opioids (endorphins, enkephalins), in addition to preventing and or reducing edema of operated tissues.

The frequency close to 100 Hz, with pulse width (duration) close to 1 ms, particularly applied close to the place of origin of the pain, is capable of allowing the sensation of immediate pain relief or blocking pain prior to an invasive procedure (such as dental drilling, dental preparation for prosthesis, removal of cavities, among others) without the feeling of numbness or tingling and, therefore, more suitable for routine of non-surgical procedures in dentistry or other areas.

Frequency close to 1000 Hz, with pulse width (duration) close to 1 ms, particularly applied close to the place of origin of the pain, is capable of allowing the sensation of immediate pain relief or blocking of pain prior to an invasive procedure surgical (cutting soft tissues, making tattoos on the skin, among others) with the feeling of numbness or tingling of the tissue and, therefore, more suitable for surgical procedures in dentistry or other areas.

As highlighted in the present invention, the combination of high and low frequency, simultaneously in different locations of the body, with adequate wave pulse duration, and rectangular waveform, with inverted exponential, allows a long-lasting and effective sensation of analgesia.

On the other hand, the non-polarized waves prevents the electrolysis of the tissues and, for this reason, the use of the device can last for more than 60 (sixty) minutes, without any type of side effect to the applied tissues, consequently, allows long-term therapy safely.

Still, the combination of low and high frequencies, particularly at different points, at a pulse width between 1 ms and 2 ms is able to produce the release of serotonin, which is considered as the pleasure transmitter and well-being hormone, in addition to helping regulation of dopamine, responsible for memory, mood and can help control addictions.

This combination of frequencies for periods of more than 20 minutes of stimulation produces a powerful analgesic effect by ascending pathways medullary block or trigeminal ganglion block, and by modulation of the neuromatrix of pain in the upper central pathways, descending and spinal block pathways by inhibitory interneurons in addition to the release of pain blocking neurotransmitters, such as enkephalins, dynorphins and GABA, already described in the literature.

Thus, the electrodes can be connected to the electro-stimulator at the pain site and at specific points on the body, such as acupuncture points of pain control command At that moment the electro-stimulator button is pressed, turning into a light ON mode indicator, then the pre-programmed frequency, waveform and pulse width appear on a display (in the equipment not shown); this done, the user presses the button again to change the frequency, if desired, to obtain the frequency mode. With one more touch, the frequency is changed, configuring a cycle of 4 options.

Figure 1:
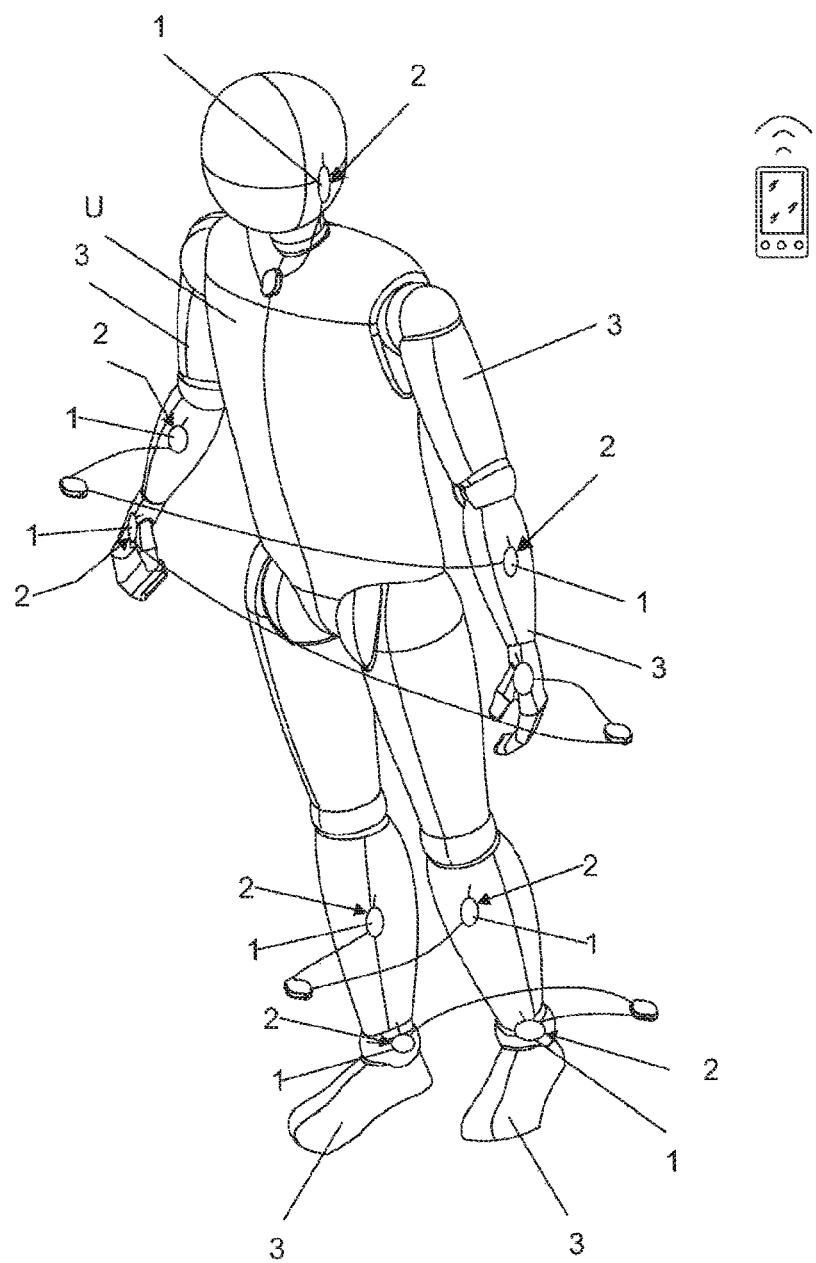
FIG. 1: Illustrative drawing of a possible user, with the application of electrodes in some points of the body.

The configuration set has the following sequence:
frequency: a two-electrode output with pre-programmable frequency (FIG. 1);
non-polarized wave, which can be alternating biphasic (FIG. 2);
pulse width: between 1 ms and 2 ms for all frequencies, except for the frequency of 1000 Hz;
ramp (ascent time): from 0 to 20 seconds;
support (plateau time): from 1 to 60 seconds;
wave with ripple: it may have ripple or not;
rest time: from 0 to 60 seconds;
mixed frequency: can have a second frequency associated;
wave amplitude: maximum peak from 0 to 100 mA output;
total application time: from 1 minute to 60 minutes;
increments: vary on a scale of 0.1 mA from 0 mA to the peak of 10 mA and then 0.5 mA variations from 10 mA to the peak of 20 mA and then increases from 1 mA from 20 mA to the peak of 100 mA.

Thus, the invention has the following general form of application:
a fast and long-lasting analgesia device;
consists of simultaneously stimulate different areas with different frequencies (0.5 Hz to 10 Hz for the release of endogenous opioids, at distal points from the pain site; medium frequency (around 15 Hz to 35 Hz) and, 80 Hz to 1000 Hz at local points or origin of the referred pain), highlighting the therapeutic intervals for pain between 0 Hz and 10 Hz, another from 15 Hz to 35 Hz, another from 80 Hz to 300 Hz and another close to 1000 Hz;
at least four electrodes must be used (two near the pain site and two at distance), and up to six can be charged at the same time in addition to the remote control;
equipment has a pulse width of 1000 µs or more, reaching 2000 µs (no TENS has this pulse width or pulse duration);
the device has an alert when the battery reaches a critical level of 20% (to allow time to plug in the electrical current) of the stimulator charge;
good battery autonomy (8 hours of work), being able to charge quickly by cable or slow charge (better for the battery) by induction charging;
retractable cables that connect the positive and negative poles to the electro-stimulator;
mini USB, USB, or USB-C type connectors on electro-stimulators for emergency charging or connection to software through computer;
remote control operating by Bluetooth to adjust the electro-stimulators, or controller by mobile phone or tablet app;
electro-stimulators with ON and OFF button, choice of pre-programmed frequencies and battery indicator;
can be connected to disposable or reusable electrodes using a "snap or push button" connector or a "pin" connector.

Thus, within the therapeutic frequency (0 to 300 Hz) the low frequencies promote long-lasting analgesia by releasing endogenous opioids (by enkephalins) and the high frequency promotes quick and short-lasting analgesia by releasing dynorphins in the location, in addition to increase the permeability of the tissues and accelerate the repair process by eliminating lactic acid and increasing the drainage flow in the region.

The device in the invention consists of a charging base for the wireless stimulator components to be coupled—it can be by wire or by induction, and must contain terminals for connection of the electro-stimulators—composed of electronic plates and rechargeable batteries—and a remote control—by Bluetooth—to control the intensity of the stimulation, on and off actions, action modes and a display for programming view and memories settled.

The invention claimed is:

1. An electroanalgesia and electrotherapy apparatus with control of command via Bluetooth or a mobile phone or tablet application, comprising: electro-stimulators generically distributed in various parts of the body, the electro-stimulators simultaneously stimulating at a pain site and at one or more points not at a pain site;
   wherein, at the pain site, the electro-stimulators emit pulses at a frequency of one or more of 80 Hz-200 Hz and 1000 Hz, the frequency of pulses at the pain site then being reduced to one or more of 15 Hz-35 Hz or 0.5 Hz-10 Hz; and
   at points not at the pain site, the electro-stimulators emit pulses at a frequency of 0.5 Hz-10 Hz;
   and wherein the apparatus uses a rectangular, non-polarized wave, with a pulse width of one or more of 1 ms and 1 ms-2 ms, and with a maximum waveform peak amplitude of 100 mA.

2. The electroanalgesia and electrotherapy apparatus according to claim 1, wherein the pulse width allows pain block.

3. The electroanalgesia and electrotherapy apparatus according to claim 1, wherein the apparatus has the following configuration:
   a frequency with an output of two electrodes at 4 types of pre-programmed frequencies and possible to be alternated during operation, without interruption of the electric current;
   a non-polarized wave;
   a pulse duration between 1 ms and 2 ms for all frequencies, except 1000 Hz;
   a ramp (ascent time) from 0 to 20 seconds;
   a support (plateau time) from 1 to 60 seconds;
   a wave with ripple;
   a rest time from 0 to 60 seconds;
   a mixed frequency;
   a wave amplitude maximum peak from 0 to 100 mA output;
   a total application time from 1 minute to 60 minutes; and
   increments vary on a scale of 0.1 mA from 0 mA to the peak of 10 mA, a scale of 0.5 mA from 10 mA to the peak of 20 mA, and at a scale of 1 mA from 20 mA to the peak of 100 mA.

4. The electroanalgesia and electrotherapy apparatus according to claim 1, wherein the rectangular, non-polarized wave is alternating biphasic.

5. The electroanalgesia and electrotherapy apparatus according to claim 2, wherein the non-polarized wave is alternating biphasic.

* * * * *